United States Patent [19]

Katz et al.

[11] Patent Number: 4,513,136
[45] Date of Patent: * Apr. 23, 1985

[54] PROCESS FOR RECOVERING CAFFEINE FROM ACTIVATED CARBON

[75] Inventors: Saul N. Katz, Monsey; George E. Proscia, West Sayville, both of N.Y.

[73] Assignee: General Foods Corporation, White Plains, N.Y.

[ * ] Notice: The portion of the term of this patent subsequent to Nov. 3, 1998 has been disclaimed.

[21] Appl. No.: 484,354

[22] Filed: Apr. 18, 1983

Related U.S. Application Data

[63] Continuation of Ser. No. 306,276, Sep. 28, 1981, abandoned, which is a continuation-in-part of Ser. No. 159,724, Jun. 16, 1980, Pat. No. 4,298,736.

[51] Int. Cl.$^3$ ............................................. C07D 473/12
[52] U.S. Cl. ..................................... 544/275; 544/274
[58] Field of Search ......................... 544/274, 275, 276

[56] References Cited

U.S. PATENT DOCUMENTS

| | | | |
|---|---|---|---|
| 2,391,981 | 1/1946 | Kremers | 260/256 |
| 4,081,563 | 3/1978 | Hudak et al. | 544/275 |
| 4,298,736 | 11/1981 | Katz et al. | 544/274 |

FOREIGN PATENT DOCUMENTS

| | | |
|---|---|---|
| 2206706 | 8/1973 | Fed. Rep. of Germany . |
| 2716798 | 10/1977 | Fed. Rep. of Germany . |
| 78586 | 12/1970 | German Democratic Rep. . |

OTHER PUBLICATIONS

Chemical Abstracts, Vol. 54, 1960, col. 12720 f–h.

*Primary Examiner*—Nicholas S. Rizzo
*Attorney, Agent, or Firm*—Basam E. Nabulsi; Thomas R. Savoie; Daniel J. Donovan

[57] ABSTRACT

The recovery of caffeine from activated carbon is accomplished according to the present invention by employing an aqueous acetic acid solution, preferably having a concentration of between about 50 and 80%, by weight, and which is capable of competing for the active sites on the carbon occupied by the caffeine to displace at least a portion of the caffeine which is then dissolved in the solvent. After the desired period of contact, preferably at a temperature above 100° C., the caffeine is separated from the solution.

5 Claims, No Drawings though the acetic acid solution does not normally boil because of elevation of the boiling point as solids dissolve in it. Generally, temperatures in the range of between about 100° C. and 130° C. are used.

PROCESS FOR RECOVERING CAFFEINE FROM ACTIVATED CARBON

DESCRIPTION

Cross-Reference to Related Applications

This application is a continuation of application Ser. No. 306,276, filed Sept. 28, 1981, abandoned, which application is a continuation-in-part of our application Ser. No. 159,724, filed June 16, 1980, now U.S. Pat. No. 4,298,736, and entitled "Carbon-Caffeine Separation."

TECHNICAL FIELD

The present invention relates to decaffeination, and particularly to an improved process for recovering caffeine from an activated carbon adsorbent.

The decaffeination of vegetable materials and vegetable material extracts is of major commercial importance. Also significant is the recovery and sale of the caffeine removed from vegetable sources such as coffee and tea. It is known that activated carbon is a good adsorbent in caffeine recovery and purification procedures, but the carbon tends to hold the caffeine so tenaciously that, often, significant quantities of caffeine are lost or reduced in commercial value. Moreover, the carbon itself has commercial value since if it is regenerated it may again be employed in caffeine recovery and purification processes. The techniques currently available to the art for separating the caffeine from the carbon have not been wholly satisfactory in terms of both degree and quality of caffeine recovery. Further, inefficient separation of caffeine from the carbon results in difficulties in carbon regeneration.

BACKGROUND ART

The recovery of caffeine from decaffeinating solvents has been an active area of concern for many years. For example, in U.S. Pat. No. 2,508,545, Shuman discloses that activated carbon and other adsorbents had been used to remove impurities from solutions of caffeine extracted from coffee. Shuman indicates that until the time of his invention caffeine losses due to adsorption onto the carbon ran as high as 10 to 14%. To rectify this, Shuman disclosed alternate use of organic and aqueous extractions with the final aqueous extraction being done at a pH of at least 7. While activated carbon is employed to remove impurities from the aqueous extract, the amounts employed are apparently small and no mention of separating caffeine from the carbon is made. Similarly, in U.S. Pat. No. 2,472,881, Bender employs activated carbon to remove impurities from an aqueous caffeine solution but does not discuss the steps taken to recover the caffeine adsorbed on the carbon.

Recently, an improved decaffeination method was disclosed by Vitzthum et al. in U.S. Pat. No. 3,879,569 wherein quantitative extraction of caffeine from raw coffee beans is achieved with moist supercritical carbon dioxide. This process produces a caffeine containing carbon dioxide stream from which essentially all of the caffeine can be removed by activated carbon. Unfortunately, the prior art techniques do not economically provide good levels of recovery of caffeine from the activated carbon or they require the use of chlorinated hydrocarbon solvents which are otherwise avoided by the use of carbon dioxide as an extractant.

The use of a treated activated carbon adsorbent in a decaffeination process has been described. Recovery of caffeine from the activated carbon employed therein is desired as is also recycling and regeneration of the carbon itself.

In our copending application Ser. No. 159,724, filed June 16, 1980, of which this application is a continuation-in-part, now U.S. Pat. No. 4,298,736, we describe and claim a process for recovering caffeine from activated carbon comprising contacting the carbon with an organic acid or an alcohol. Acetic acid and acetic acid azeotropes are especially preferred as the solvents. However, when glacial acetic acid is employed operational and safety problems arise because of the low (104° F.) flashpoint of glacial acetic acid and of its causing burns of the skin.

DISCLOSURE OF INVENTION

The present invention now enables the recovery of caffeine from an activated carbon adsorbent by an improved process which comprises: contacting activated carbon having caffeine adsorbed thereon with an aqueous acetic acid solution, preferably having a concentration of between about 50 and 80%, by weight, and most preferably having a concentration of about 70%, by weight, and which is capable of displacing at least a portion of the caffeine from active sites on the carbon; maintaining the contact for a period of time and at a temperature effective for the acetic acid solution to displace at least a portion of the caffeine from the carbon and dissolve the displaced caffeine; and separating the caffeine from the acetic acid solution.

This invention is based on the discovery that acetic acid water mixtures, preferably having a concentration of between about 50% and 80%, by weight, may be employed to elute either batchwise or continuously in a countercurrent manner the caffeine and other solids from the spent activated carbon. Although acetic acid-water mixtures are usually less efficient than pure glacial acetic acid they offer the advantage of being totally non-flammable with no flashpoint. Glacial acetic acid is flammable with a flashpoint of 104° F. Flammable solvents require equipment that is explosion-proof and proper safe buildings. These requirements significantly increase the capital costs for the process. By adding water to glacial acetic acid or using acetic acid-water mixtures this requirement is eliminated and thereby dramatically reduces capital costs. Most preferably, acetic acid of 70% concentration which is commercially available is used.

The present invention also takes advantage of the discovery that acetic acid has the ability to effect desorption both by its strong solvent ability and its ability to displace the adsorbed material from active sites on the adsorbent and is extremely effective in separating caffeine from activated carbon. The strong solvent effect causes a partitioning between the activated carbon and the acetic acid. The site displacement effect is achieved by the acetic acid molecules themselves competing for the active adsorbent sites. Once a caffeine molecule is displaced, it is then taken into solution by the acetic acid solution which is a strong solvent for caffeine.

The acetic acid solution is employed according to the present invention at temperatures in excess of 100° C. to obtain the greatest rates of recovery of caffeine. Temperature has a strong effect on desorption and should therefore be as high as possible, consistent with maintaining the acetic acid solution as a liquid. Where temperatures higher than the boiling point of the acetic acid solution are desired, it will be necessary to employ pressures in excess of atmospheric.

Because the caffeine is valuable for food and pharmaceutical use, the acetic acid must be foodgrade. The acetic acid solution is liquid at the proposed processing temperature and at room temperature, is an excellent solvent for caffeine, is capable of displacing caffeine from the active sites on the carbon and is an especially effective solvent for use according to the invention since it eliminates the flammability problem which may arise with glacial acetic acid. Preferably, the acetic acid solution has a concentration of about 50 to 80%, and most preferably 70%, by weight.

The acetic acid solution is maintained in contact with the carbon having caffeine adsorbed thereon for a period of time and at a temperature effective for the solvent to displace at least a portion of the caffeine from the carbon and dissolve the displaced caffeine. As noted above, preferred temperatures will be above 100° C., but the specific temperature for any particular process will be selected on its own set of economic considerations and may be below this. Practical contact times will be determined on the basis of the desired degree of recovery and the desorption rate for a particular system. Preferably, the contact time should be sufficient to permit displacement (recovery) of at least 80% by weight of the caffeine from the carbon and into solution with the acetic acid solution. Because the caffeine is valuable as a product and, if not removed from the carbon, decreases the adsorbent capacity of the carbon, higher rates of displacement, on the order of 90% by weight or more, are desired.

As the activated carbon adsorbent can be any of those types commercially available which are effective caffeine adsorbents and capable of withstanding the rigors of recycling permitted by the invention. Preferred activated carbons are those prepared from coconut, coal and lignite, particularly those available commercially from Calgon Corporation, ICI, Carborundum and Union Carbide Corporation.

After contact for the requisite period of time, the activated carbon is preferably separated from the acetic acid solution prior to separation of the caffeine from the solvent. The simplest and most effective manner for removing the carbon from the solution is by filtration.

The caffeine may also be separated from the solution. The caffeine which is recovered is generally of about 20 to 25% purity. The caffeine may be converted to U.S.P. caffeine by techniques of dissolution, crystallization, solvent purification and the like.

The activated carbon may be regenerated by washing and steaming to remove residual acetic acid. The activated carbon may then be reused through several more decaffeination cycles before reactivation, usually by means of thermal reactivation, is required.

BEST MODE FOR CARRYING OUT THE INVENTION

The following examples are for the purpose of illustrating and explaining the best mode for carrying out the invention, but are not meant to be limiting in any regard. Unless otherwise indicated, all parts and percentages are by weight.

EXAMPLE 1

One hundred parts of 70% acetic acid solution and 10 parts of activated carbon pellets containing 9.1% by weight caffeine, obtained from the process of U.S. Pat. No. 3,879,569, of Vitzthum et al. were introduced into a Soxhlet extraction tube and then refluxed at atmospheric pressure and 110° C. for 16 hours. The caffeine was recovered from the solution by evaporation. The total amount of caffeine recovered was 0.91 parts, 100% recovery.

EXAMPLE 2

A pilot plant multi-column system run was made with three columns on stream at all times. The activated carbon had been employed to decaffeinate green coffee bean extract. Sixty pounds of the spent activated carbon containing 5.7% caffeine, dry basis, were contacted with a 70% acetic acid solution. An 83% recovery of caffeine was achieved after four cycles. The draw-off acetic acid solution, approximately 225 pounds, contained 2.7 pounds of caffeine of 29% purity.

The conditions for the run were as follows:

| Acetic Acid Concentration, % | 70 |
|---|---|
| Temperature | 300° F. (150° C.) |
| Pressure | 85 psig |
| Flow Rate | 30 lbs/hr (210 cc/min) |
| $\frac{\text{Lbs. Acetic Acid}}{\text{Lbs. Spent Carbon}}$ (Ratio) | 5.0 |
| Cycle Time | 10.0 Hours |

The columns used were 4" diameter × 20' height. All tanks in use had been sealed to avoid any vapor loss to the atmosphere—they were also connected to condenser lines to avoid buildup of pressure in case of excess vapor formation.

The acetic acid-caffeine crude produced during the run was processed by evaporation of the acetic acid followed by steam stripping and standard caffeine solvent treatment of the sludge. Refined caffeine, of 88% purity, was obtained.

The carbon was subsequently reactivated by thermal means.

The following table indicates cumulative caffeine recoveries.

TABLE
CUMULATIVE % CAFFEINE RECOVERED FROM SPENT CARBON

| | % Acetic Acid in Solution | | | | |
|---|---|---|---|---|---|
| Stage | 60 | 70 | 80 | 90 | 100 |
| 1 | 38.0 | 45.7 | 54.3 | 58.7 | 59.8 |
| 2 | 58.6 | 67.4 | 76.1 | 79.3 | 76.2 |
| 3 | 70.7 | 79.3 | 85.9 | 90.2 | 86.5 |
| 4 | 78.3 | 85.7 | 90.2 | 93.5 | 90.2 |
| 5 | 82.6 | 90.4 | 92.5 | 95.7 | 91.3 |

Note: Each stage had 10/1 fresh acetic acid solution/initial spent carbon.

The above description has been for the purpose of teaching a person skilled in the art how to practice the invention. It is not intended to describe in detail each and every modification and variation of the invention which will become apparent to those skilled in the art upon study. It is intended, however, that all such modifications and variations be included within the scope of the invention as defined by the following claims.

We claim:
1. A process for recovering caffeine from activated carbon comprising:
   contacting activated carbon having caffeine adsorbed thereon with an aqueous acetic acid solution hav- ing a concentration of between about 50% and 80%, by weight, and which is capable of displacing at least a portion of the caffeine from active sites on the carbon;

maintaining the contact for a period of time, and at a temperature of at least 100° C., effective for the solution to displace at least a portion of the caffeine from the carbon and dissolve and displaced caffeine;

separating the carbon from the solution; and recovering the caffeine from the solution by steam distilling the solution or evaporating the solution.

2. A process according to claim 1 wherein the contact is maintained at a pressure in excess of atmospheric.

3. A process according to claim 1 wherein contact is maintained for a period of time sufficient to permit displacement of at least 80% by weight of the caffeine from the carbon and into solution with the acetic acid solution.

4. A process according to claim 3 wherein the carbon is separated from the solution by decantation prior to separating the caffeine from the solution.

5. A process according to claim 1 wherein the caffeine is further purified and refined and the carbon is regenerated and/or reactivated.

* * * * *